(12) United States Patent
Struelens et al.

(10) Patent No.: US 11,987,769 B2
(45) Date of Patent: May 21, 2024

(54) BRANCHED FATTY ACIDS AND ESTERS THEREOF

(71) Applicant: OLEON NV, Evergem (BE)

(72) Inventors: Pieter Struelens, Gooik (BE); Andreas Lambin, Antwerp (BE); Dirk Packet, Rotselaar (BE)

(73) Assignee: OLEON NV, Evergem (BE)

( * ) Notice: Subject to any disclaimer, the term of this patent is extended or adjusted under 35 U.S.C. 154(b) by 720 days.

(21) Appl. No.: 17/053,580

(22) PCT Filed: May 3, 2019

(86) PCT No.: PCT/EP2019/061464
§ 371 (c)(1),
(2) Date: Nov. 6, 2020

(87) PCT Pub. No.: WO2019/215054
PCT Pub. Date: Nov. 14, 2019

(65) Prior Publication Data
US 2021/0230505 A1    Jul. 29, 2021

(30) Foreign Application Priority Data
May 7, 2018  (EP) .................................... 18171110

(51) Int. Cl.
| | |
|---|---|
| A61K 31/23 | (2006.01) |
| A61K 8/36 | (2006.01) |
| A61K 31/185 | (2006.01) |
| A61Q 17/04 | (2006.01) |
| A61Q 19/00 | (2006.01) |
| C10M 129/32 | (2006.01) |
| C11C 3/08 | (2006.01) |
| C11C 3/14 | (2006.01) |
| C10N 20/00 | (2006.01) |

(52) U.S. Cl.
CPC ................ *C11C 3/14* (2013.01); *A61K 8/361* (2013.01); *A61Q 17/04* (2013.01); *A61Q 19/00* (2013.01); *C10M 129/32* (2013.01); *C11C 3/08* (2013.01); A61K 2800/10 (2013.01); C10M 2207/126 (2013.01); C10N 2020/011 (2020.05); C10N 2020/071 (2020.05)

(58) Field of Classification Search
CPC .............................. A61K 31/23; A61K 31/185
USPC ................................................. 514/552, 557
See application file for complete search history.

(56) References Cited

U.S. PATENT DOCUMENTS

| | | | |
|---|---|---|---|
| 4,028,385 | A | 6/1977 | Fujita et al. |
| 2015/0119598 | A1 | 4/2015 | Kinsho et al. |
| 2015/0291912 | A1 | 10/2015 | Bergen-Brenkman et al. |

FOREIGN PATENT DOCUMENTS

| | | | |
|---|---|---|---|
| EP | 1782789 | A1 | 5/2007 |
| EP | 2702127 | B1 | 6/2015 |
| JP | S5129436 | A | 3/1976 |
| JP | 2000511213 | A | 8/2000 |
| JP | 2007505194 | A | 3/2007 |
| JP | 2009062364 | A | 3/2009 |
| JP | 2015506342 | A | 3/2015 |
| JP | 2015110554 | A | 6/2015 |
| JP | 2016501836 | A | 1/2016 |
| KR | 20130093891 | A | 8/2013 |
| WO | 9743361 | A1 | 11/1997 |
| WO | 2005026300 | A1 | 3/2005 |
| WO | 2006003992 | A1 | 1/2006 |
| WO | 2013093411 | A1 | 6/2013 |
| WO | 2014064418 | A2 | 5/2014 |

OTHER PUBLICATIONS

English language translation of Haase et al., (Zusammensetzung und Anwendungen von Isostearinsaure FETT-LIPID, Fat Science Technology, vol. 91, No. 9, Jan. 1989, pp. 350-353. (Year: 1989).*
Haase, et al., "Zusammensetzung und Anwendungen von Isostearinsäure" FETT-LIPID. Fat Science Technology, vol. 91, No. 9, Jan. 1989, pp. 350-353 (with English-language Abstract).
Nakano, et al., "Thermal Alteration of Oleic Acid in the Presence of Clay Catalysts with Co-Catalysts," JAOCS, vol. 62, No. 5, May 1985, pp. 888-891.
International Search Report issued in PCT/EP2019/061464, dated Jul. 2, 2019, pp. 1-3.

\* cited by examiner

*Primary Examiner* — Raymond J Henley, III
(74) *Attorney, Agent, or Firm* — ARENTFOX SCHIFF LLP

(57) ABSTRACT

The present invention relates to a composition of branched fatty acids or esters thereof, the process for preparing such a composition and its use in various industrial fields, such as in lubricant, in cosmetics and in home care. More particularly, the present invention relates to a composition comprising at least 30% by weight of polybranched $C_{10}$-$C_{24}$ fatty acids or esters thereof, and a cyclic compound content ranging from 1% to 8% by weight, the weight percentage being given on the total weight of the composition.

16 Claims, No Drawings

BRANCHED FATTY ACIDS AND ESTERS THEREOF

CROSS-REFERENCE TO RELATED APPLICATIONS

This application is a National Stage Entry of PCT/EP2019/061464, filed May 3, 2019, which claims priority to EP application No. 18171110.2, filed May 7, 2018, the disclosures of each of which are hereby incorporated by reference in their entireties.

The present invention relates to a composition of branched fatty acids or esters thereof, the processes for preparing such compositions and their uses in various industrial fields, such as in a lubricant, in a personal care and in a home care composition.

Commercially available branched fatty acids such as "isostearic acid" are obtained as a by-product of the catalytic and thermal dimerization of unsaturated linear fatty acid(s). Dimer and higher oligomer acids are produced by heating unsaturated fatty acid(s) in the presence of a catalyst. But instead of oligomerizing, a portion of the fatty acid(s) rearranges to give branched monomeric fatty acids which can be isolated from the oligomerized fatty acids. This branched fatty acids composition commercially known as "isostearic acid" is a mixture of various linear and mainly branched, both mono and polybranched, saturated monocarboxylic fatty acids.

During the last years, focus shifted to optimization of production of those branched monomeric fatty acids, no more considered as by-product. In particular, esters derived from "isostearic acid" are widely used in lubricant and cosmetic compositions.

EP 2 702 127 describes a process for producing monobranched fatty acids via isomerization of unsaturated $C_{10}$-$C_{26}$ fatty acids in the presence of a catalyst which comprises both a zeolite and a Lewis base.

The Applicant surprisingly found that a composition comprising a high content of polybranched $C_{10}$-$C_{24}$ fatty acids or esters thereof and a reduced cyclic compound content leads to better low temperature properties, particularly regarding its cloud and pour point. The aforementioned prior art document is silent with regards to this cyclic compound content.

Accordingly, the present invention relates to a composition having a high content of polybranched fatty acids or esters thereof and a low content of cyclic compounds.

More particularly, the present invention relates to a composition of branched $C_{10}$-$C_{24}$ fatty acids or esters thereof, comprising:
  at least 30% by weight of polybranched $C_{10}$-$C_{24}$ fatty acids or esters thereof, and
  1 to 8% by weight of cyclic compounds, weight % being given on the total weight of the composition.

In the present application, unless otherwise indicated, all ranges of values used are to be understood as being inclusive limits.

Advantageously, the composition of the present invention is more stable.

Advantageously, the composition of the invention is liquid at 0° C. due to polybranched fatty acids and less cyclic compounds. This composition is also stable at high temperatures and resists UV radiation.

Advantageously, the composition of the present invention exhibits better low temperature properties. Pour points of the present composition of branched $C_{10}$-$C_{24}$ fatty acid esters can be less than −40° C., which is lower than the pour point of corresponding esters obtained from a commercial composition of branched fatty acids as shown in Example 2.

By "branched" fatty acid, it is intended that the hydrocarbon chain of the monocarboxylic fatty acid bears one or more alkyl side group(s), which is/are generally short.

By "short alkyl side group", it is intended a group comprising less than 5 carbon atoms. More particularly, each short alkyl side group is linear and still more particularly, is chosen among the group constituted by methyl, ethyl and propyl. Preferably each short alkyl side group is a methyl and/or an ethyl, more preferably a methyl.

By "branched $C_{10}$-$C_{24}$ fatty acids or esters thereof", it is then intended polybranched $C_{10}$-$C_{24}$ fatty acids or esters of polybranched $C_{10}$-$C_{24}$ fatty acids, and optionally monobranched $C_{10}$-$C_{24}$ fatty acids or esters of monobranched $C_{10}$-$C_{24}$ fatty acids, respectively.

By "monobranched" fatty acid, it is intended that the linear hydrocarbon chain of the fatty acid bears only one alkyl side group, which is generally short.

By "polybranched" fatty acid, it is intended that the linear hydrocarbon chain of the fatty acid bears two or more alkyl side groups, which are generally short.

In the term "$C_X$", x indicates the number of carbon atoms in the fatty acid, in other words, the number of carbon atoms in the hydrocarbon chain plus the optional alkyl side group(s). Consequently, "branched $C_X$" designate all the branched fatty acids having X carbon atoms. In particular, these branched fatty acids are position isomers.

By "$C_X$-$C_Y$ fatty acids or esters thereof", it is then intended that the number of carbon atoms in each fatty acid is comprised independently between X and Y.

The polybranched fatty acids or esters thereof are saturated monocarboxylic fatty acids or esters thereof.

Preferably, polybranched $C_{10}$-$C_{24}$ fatty acids or esters thereof, are polybranched $C_{14}$-$C_{22}$ fatty acids or esters thereof, more preferably polybranched $C_{16}$-$C_{18}$ fatty acids or esters thereof.

In a specific embodiment, the composition of branched $C_{10}$-$C_{24}$ fatty acids or esters thereof according to the invention comprises at least 30% by weight of polybranched $C_{18}$ fatty acids or esters thereof, based on the total weight of the composition.

Preferably the composition comprises at least 32% by weight, more preferably at least 34% by weight, of polybranched $C_{10}$-$C_{24}$ fatty acids or esters thereof, based on the total weight of the composition.

The ester of $C_{10}$-$C_{24}$ fatty acids may be a monoester or a polyester. Indeed, the ester composition according to the invention can be obtained by esterification of the $C_{10}$-$C_{24}$ fatty acid composition with an alcohol that may be a monohydroxyl, a polyhydroxyl or a mixture thereof. Preferably, the alcohol consists of a saturated linear or branched hydrocarbon chain comprising one or more hydroxyl(s).

"Cyclic compounds" include but are not limited to alicyclic carboxylic acids or esters thereof, aromatic(s), alkylcyclopentanone(s), lactone(s) and mixture thereof.

By "alicyclic carboxylic acid or ester thereof", it is intended a molecule comprising one carboxylic acid or an ester function, one cyclic hydrocarbon and one or more linear hydrocarbon chain(s). Preferably, the alicyclic carboxylic acid or ester thereof is saturated. Preferably, the cyclic hydrocarbon is a cyclopentyl or a cyclohexyl. More particularly, the alicyclic carboxylic acid or ester thereof is of formula (I) and/or (II):

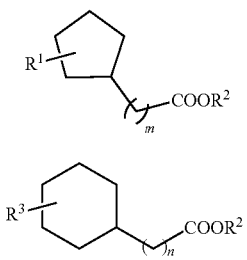

(I)

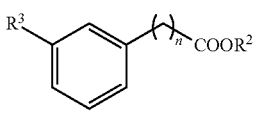

(II)

wherein:
R¹ is an hydrocarbon chain comprising 0-18, preferably 0-12 carbon atoms;
R³ is an hydrocarbon chain comprising 0-17, preferably 0-11 carbon atoms;
R² is an hydrogen or an hydrocarbon chain eventually substituted by an hydroxyl group or an ester function;
m is an integer comprised between 0 and 18, preferably between 1 and 12;
n is an integer comprised between 0 and 17, preferably between 1 and 11.

Aromatic(s) include but are not limited to phenyl carboxylic acid(s) or ester(s) thereof.

By "phenyl carboxylic acid or ester thereof", it is intended a molecule comprising a carboxylic acid or an ester function, and a phenyl group.

In particular, the phenyl carboxylic acid or ester thereof is of formula (III):

(III)

wherein:
R³ is an hydrocarbon chain comprising 0-17, preferably 0-11 carbon atoms;
R² is an hydrogen or an hydrocarbon chain eventually substituted by an hydroxyl group or an ester function;
n is an integer comprised between 0 and 17, preferably between 1 and 11.

More particularly, the phenyl carboxylic acid or ester thereof is of formula (III), wherein R¹ is hydrocarbon chain comprising 3 carbon atoms and n is equal to 9.

Preferably, the cyclic compounds comprise from 14 to 22 carbon atoms, more preferably from 16 to 18 carbon atoms.

Preferably, the cyclic compound content ranges from 1% to 6% by weight, more preferably from 3% to 5% by weight, based on the total weight of the composition.

Preferably, cyclic compounds of the composition of the invention comprise alicyclic carboxylic acid(s) or ester(s) thereof, which content ranges from 0.5% to 6% by weight based on the total weight of the composition.

Advantageously, the alicyclic carboxylic acid(s) or ester(s) thereof content ranges from 0.5% to 4%, more preferably ranges from 0.5% to 3%, still more preferably ranges from 1% to 2.5% by weight, based on the total weight of the composition.

Advantageously, the composition according to the invention comprises less than 3% by weight of aromatic(s), preferably less than 2.5%, more preferably less than 2.3%, even more preferably less than 2% by weight of aromatic(s), based on the total weight of the composition.

Typically, the composition of the invention comprises from 0.2% to 2.3%, more preferably from 0.2% to 1.8% by weight of aromatic(s), based on the total weight of the composition.

Preferably, the alkylcyclopentanone content is less than 1%, more preferably less than 0.6% by weight, based on the total weight of the composition.

Preferably, the lactone content is less than 2%, more preferably less than 1.5%, still more preferably less than 1% by weight, based on the total weight of the composition.

Advantageously, the composition of the invention comprises at least 15% by weight of monobranched $C_{10}$-$C_{24}$ fatty acids or esters thereof, based on the total weight of the composition.

The monobranched fatty acids or esters thereof, are saturated monocarboxylic acids or esters thereof.

Preferably, the composition according to the invention comprises at least 25% by weight, more preferably at least 30% by weight of monobranched $C_{10}$-$C_{24}$ fatty acids or esters thereof, based on the total weight of the composition.

Preferably, monobranched $C_{10}$-$C_{24}$ fatty acids or esters thereof, are monobranched $C_{14}$-$C_{22}$ fatty acids or esters thereof, more preferably monobranched $C_{16}$-$C_{18}$ fatty acids or esters thereof.

In particular, the composition according to the invention comprises at least 15% by weight of monobranched $C_{18}$ fatty acids or esters thereof, based on the total weight of the composition.

Advantageously, the weight ratio monobranched/polybranched $C_{18}$ fatty acids or esters thereof, of the composition of the invention, ranges from 0.5 to 1.5. Preferably, the weight ratio ranges from 0.5 to 1.4 more preferably from 0.6 to 1.3.

Advantageously, the composition of the invention comprises at least 50% by weight of mono and polybranched $C_{10}$-$C_{24}$ fatty acids or esters thereof, based on the total weight of the composition.

Preferably, the composition of the invention comprises at least 60% by weight, more preferably at least 70% by weight, still more preferably at least 80% by weight of mono and polybranched $C_{10}$-$C_{24}$ fatty acids or esters thereof, based on the total weight of the composition.

In a specific embodiment, the composition comprises at least 60% by weight, preferably at least 68%, more preferably at least 70% by weight of mono and polybranched $C_{18}$ fatty acids or esters thereof, based on the total weight of the composition.

Advantageously, the composition of the invention further comprises 1-25% by weight of linear saturated $C_8$-$C_{24}$ fatty acid(s) or ester(s) thereof, based on the total weight of the composition.

Preferably, the linear $C_8$-$C_{24}$ fatty acid(s) or ester(s) thereof content ranges from 1% to 20%, more preferably from 5% to 18% by weight, based on the total weight of the composition.

Preferably, the composition according to the invention comprises less than 18%, preferably less than 16% by weight of linear 016 fatty acid or ester thereof, based on the total weight of the composition.

In a preferred embodiment, the composition of the invention comprises:
30-60% by weight of polybranched $C_{10}$-$C_{24}$ fatty acids or esters thereof;
15-50% by weight of monobranched $C_{10}$-$C_{24}$ fatty acids or esters thereof;

5-18% by weight of linear $C_8$-$C_{24}$ fatty acid(s) or ester(s) thereof;

0.5-3% by weight of alicyclic carboxylic acid(s) or ester(s) thereof; the weight % being with respect to the total weight of the composition, and wherein the weight ratio monobranched/polybranched 018 fatty acids or esters thereof, ranges from 0.5 to 1.5, preferably from 0.6 to 1.3.

In particularly preferred embodiment, the composition of the invention comprises:
- 30-40% by weight of polybranched $C_{18}$ fatty acids or esters thereof;
- 25-45% by weight of monobranched $C_{18}$ fatty acids or esters thereof;
- 4-18% by weight of branched Cm fatty acids or esters thereof;
- 5-18% by weight of linear $C_8$-$C_{24}$ fatty acid(s) or ester(s) thereof;
- 0.5-3% by weight of alicyclic carboxylic acid(s) or ester(s) thereof; the weight % being with respect to the total weight of the composition, and wherein the weight ratio monobranched/polybranched $C_{18}$ fatty acids or esters thereof, ranges from 0.5 to 1.5, preferably from 0.6 to 1.3.

This particularly preferred embodiment of the composition of the present invention exhibits very good low temperature properties. More particularly, the cloud point is less than 5° C. and more particularly less than 3° C. It is an advantage to provide a low cloud point composition, as the cloud point refers to the temperature below which the composition exhibits solid particles which may not be desirable for the consumer eye and may result in plugging small orifices.

On the contrary, commercial composition of branched fatty acids, such as Radiacid 0907 from Oleon, has a cloud point of about 7° C., determined by method AOCS Cc 6-25.

The invention also relates to a process for preparing a composition of branched $C_{10}$-$C_{24}$ fatty acids from a starting material comprising at least 70% by weight of linear monoethylenically unsaturated $C_{10}$-$C_{24}$ fatty acid(s) based on the total weight of the starting material, comprising the following steps:
i) isomerizing the linear monoethylenically unsaturated $C_{10}$-$C_{24}$ fatty acid(s) from the starting material, by heating in the presence of a clay catalyst, and
ii) separating the monomeric fraction from the oligomeric fraction formed during step i)
iii) purifying the monomeric fraction to obtain the composition of branched $C_{10}$-$C_{24}$ fatty acids.

Advantageously, the process for preparing a composition of branched $C_{10}$-$C_{24}$ fatty acids according to the invention allows obtaining an high polybranched $C_{10}$-$C_{24}$ fatty acid content and a low cyclic compound content.

Step i) is performed at a sufficient temperature to achieve an isomerization reaction. The isomerizing step may be conducted at a temperature ranging from 150° C. to 300° C., preferably from 180° C. to 260° C. and at a pressure ranging from 1 barg to 10 barg, preferably from 2 barg to 8 barg.

By "barg", it is intended the unit of the gauge pressure measurement.

The isomerizing step may be conducted during 1 hour to 8 hours, preferably during 2 hours to 5 hours.

The isomerizing step may be performed in the presence of water, the water content ranging preferably from 0.1 to 5% by weight based on the total weight of the starting material.

Advantageously, in the process for preparing a composition according to the invention, the isomerization step may be conducted in the presence of up to 0.5% by weight of an alkali metal salt, weight % being given on the total weight of the starting material.

The isomerization conditions allow obtaining a monomeric fraction at a yield ranging from 40% to 70%, preferably from 55 to 70%.

The isomerizing step may be followed by an additional step of treatment with an inorganic acid, preferably with phosphoric acid.

The isomerizing step may be followed by an additional step of separation of the clay catalyst from the reaction product of step i), preferably by filtration.

Step ii) is preferably achieved by distillation, in particular by molecular distillation, at a temperature ranging from 200 to 300° C. and at a pressure ranging from 1 to 4 mbar.

Step iii) can comprise hydrogenation, crystallization and/or distillation.

Hydrogenation may be carried out by ways known in the art, for example by using palladium on carbon or supported nickel as a catalyst. Preferably, the temperature during hydrogenation ranges from 180 to 250° C. and the pressure ranges from 15 to 25 barg.

Crystallization may be carried out using sulfate salts or urea (chlatration process) to separate the resulting solidified linear fatty acids from liquid branched fatty acids.

Distillation is preferably conducted at a temperature ranging from 200 to 300° C. and at a pressure ranging from 1 to 4 mbar.

After step iii), a composition of branched $C_{10}$-$C_{24}$ fatty acids is obtained, in particular comprising at least 30% by weight of polybranched $C_{10}$-$C_{24}$ fatty acids and from 1 to 8% by weight of cyclic compounds, weight % being given on the total weight of the composition.

Linear, branched, monobranched and polybranched $C_{10}$-$C_{24}$ fatty acids and cyclic compounds are as described above, including preferential and advantageous positions.

The starting material is advantageously fatty acids of a renewable oil. A renewable oil is preferably a vegetable oil or an animal oil.

Some renewable oils comprise naturally at least 70% by weight of linear monoethylenically unsaturated $C_{10}$-$C_{24}$ fatty acid group(s) based on the weight of the renewable oil. Corresponding fatty acids may be recovered from one of these oils by any known method in the art. Suitable renewable oils are high oleic sunflower oil, oleic safflower oil, crambe oil, lunaria oil and olive oil. Preferably, the starting material is fatty acids obtained from high oleic sunflower oil, from oleic safflower oil or from crambe oil.

Some renewable oils that are mono and polyethylenically unsaturated, but comprise less than 70% by weight of linear monoethylenically unsaturated $C_{10}$-$C_{24}$ fatty acid group(s) based on the weight of the renewable oil, may be partially hydrogenated to optimize their content, prior to the recovering of corresponding fatty acids. Suitable renewable oils to partially hydrogenate are rapeseed oil, corn oil, soya bean oil, sunflower oil, safflower oil and tall oil.

Fatty acids obtained from any renewable oil may be fractionated to isolate one or more specific linear monoethylenically unsaturated $C_{10}$-$C_{24}$ fatty acid(s) and obtain an adapted starting material.

Linear monoethylenically unsaturated $C_{10}$-$C_{24}$ fatty acids are monocarboxylic acids.

Preferably, linear monoethylenically unsaturated $C_{10}$-$C_{24}$ fatty acid(s) is oleic acid, gadoleic acid, erucic acid, nervonic acid or a mixture thereof.

In a specific embodiment, in the process for preparing a composition of branched $C_{10}$-$C_{24}$ fatty acids, the starting material comprises at least 70% by weight of oleic acid based on the total weight of the starting material.

Preferably, the starting material further comprises at least 5% by weight of linear polyethylenically unsaturated $C_{10}$-$C_{24}$ fatty acid(s).

Linear polyethylenically unsaturated $C_{10}$-$C_{24}$ fatty acids are monocarboxylic acids.

Preferably, linear polyethylenically unsaturated $C_{10}$-$C_{24}$ fatty acid(s) is/are linear diethylenically unsaturated $C_{10}$-$C_{24}$ fatty acid(s), in particular linoleic acid.

In particular, the starting material is fatty acids obtained from high oleic sunflower oil.

Preferably, the starting material comprises at least 75% by weight, more preferably at least 80% by weight of linear monoethylenically unsaturated $C_{10}$-$C_{24}$ fatty acid(s), based on the total weight of the starting material.

Preferably, the starting material comprises no more than 95% by weight, more preferably no more than 90% by weight of linear monoethylenically unsaturated $C_{10}$-$C_{24}$ fatty acid(s), based on the total weight of the starting material.

The clay catalyst is preferably selected among bentonite, montmorillonite, beidellite, nontronite, saponite, hormite (attapulgite, sepiolite) or mixtures thereof.

Advantageously, in the process for preparing a composition of branched $C_{10}$-$C_{24}$ fatty acids, the clay catalyst is a bentonite.

The clay catalyst content preferably ranges from 1 to 10%, preferably from 2 to 8% by weight, based on the total weight of the starting material.

The invention also relates to a process for preparing a composition of esters of branched $C_{10}$-$C_{24}$ fatty acids comprising a step of esterifying the composition of branched $C_{10}$-$C_{24}$ fatty acids obtained according to the process for preparing a composition of branched $C_{10}$-$C_{24}$ fatty acids according to the invention.

For this esterifying step, the branched $C_{10}$-$C_{24}$ fatty acids react with an alcohol, by any known method by the person skilled in the art.

The alcohol may be a monohydroxyl, a polyhydroxyl or a mixture thereof.

Esters of linear, branched, monobranched and polybranched $C_{10}$-$C_{24}$ fatty acids are as described above, including preferential and advantageous positions.

According to the application, the person skilled in the art would choose an adapted alcohol.

The processes according to the invention allow obtaining a composition of branched $C_{10}$-$C_{24}$ fatty acids or esters thereof, wherein the weight ratio monobranched/polybranched $C_{18}$ fatty acids ranges from 0.5 to 1.5, preferably from 0.5 to 1.4, more preferably from 0.6 to 1.3.

Advantageously, the processes according to the invention allow obtaining compositions according to the invention. Thus the composition according to the invention is obtainable by the process according to the invention, which is a process economically viable.

It is useful to prepare a composition of branched fatty acid esters, as it may be added as functional ingredients in different industrial, personal or home care applications.

Therefore, for those applications and in particular for those described below, the composition according to the invention is preferably a composition of branched $C_{10}$-$C_{24}$ fatty acid esters, more particularly a composition of branched $C_{16}$-$C_{18}$ fatty acid esters.

The invention also concerns the use of the composition of the invention in a lubricant, a personal care and/or a home care composition.

Compositions according to the invention have many properties.

In particular, compositions of branched $C_{10}$-$C_{24}$ fatty acid esters, preferably compositions of branched $C_{16}$-$C_{18}$ fatty acid esters according to the invention are useful in lubricant compositions as they exhibit excellent cold stability properties.

Therefore, the invention also relates to a lubricant composition comprising the composition of the invention and a base oil.

Preferably, the base oil content is at least 50% by weight, more preferably at least 75% by weight based on the weight of the lubricant composition.

The base oil may comprise one or more oils chosen among mineral oils, renewable oils and/or synthetic oils. Preferably, the base oil is chosen from the group consisting of mineral oils and/or synthetic oils.

Mineral oils are oils obtained from petroleum refining. They consist essentially of carbon and hydrogen atoms, such as paraffinic oils, hydrorefined oils, hydrocracked oils and hydro-isomerized oils.

Mineral oils are categorized into three groups:
  group I oils: these oils have a saturated hydrocarbon content less than 90% by weight, an aromatic hydrocarbon content higher than 1.7% by weight, a sulfur content higher than 0.03% by weight, and a viscosity index between 80 and 120;
  group II oils: these oils have a saturated hydrocarbon content higher than 90% by weight, an aromatic hydrocarbon content less than 1.7% by weight, a sulfur content less than 0.03% by weight, and a viscosity index between 80 and 120;
  group III oils: these oils have a saturated hydrocarbon content higher than 90% by weight, an aromatic hydrocarbon content less than 1.7% by weight, a sulfur content less than 0.03% by weight, and a viscosity index higher than 120; weight percentages being based on the weight of the oil.

Synthetic oils are obtained by chemical reaction between molecules of petrochemical origin and/or of renewable origin, with the exception of the usual chemical reactions used to obtain mineral oils (such as hydrorefining, hydrocracking, hydrotreating). hydroisomerization, etc.). Examples of synthetic oils, are esters, polyalkylene glycols (PAG) and polyalphaolefins (PAO). Preferably, synthetic oil is a polyalkylene glycol (PAG) a polyalphaolefin (PAO) or a mixture thereof.

Lubricant compositions of the invention find advantageously applications in the industrial sector, the automotive sector, the maritime sector and the metalworking sector.

Examples of lubricant compositions of industrial sector are textile fiber oils, industrial transmission oils, compressor oils, turbine oils, gear oils and hydraulic oils.

Examples of lubricant compositions of automotive sector are hydraulic oils, transmission fluids, cooling fluids, engine oils, oils for axles, gearbox fluids, brake fluids, shock-absorber oils and damper oils.

Examples of lubricant compositions of maritime sector are stern tube oils and thruster oils.

In the present patent application, the terms "oil" and "fluid" are used interchangeably in the designation of the applications/uses of the compositions according to the invention.

Examples of lubricant compositions of metalworking sector, which are also named metalworking oils or metalworking fluids, are rolling oils, cutting oils, grinding oils, quenching oils, drawing and stamping oils and casting oils.

Preferably, the composition according to the invention can be used for the preparation of a lubricant composition for the automotive sector and/or for the industrial sector.

A composition according to the invention, in particular a composition of branched $C_{10}$-$C_{24}$ fatty acid esters, can also be used in a crude oil emulsion demulsification process. In particular, esters obtained by the process for preparing a composition of esters of branched $C_{10}$-$C_{24}$ fatty acids according to the invention, wherein the esterifying step is performed using trimethylolpropane as alcohol, allow a demulsification faster than corresponding esters obtained from commercial branched fatty acids.

In cosmetics, in particular in personal care compositions, compositions according to the invention, in particular compositions of branched $C_{10}$-$C_{24}$ fatty acid esters, are also useful as they exhibit very good stability properties, in particular against oxidation and/or temperature.

Compositions according to the invention form a film on skin with a very good permeability property.

Advantageously, a composition of branched $C_{10}$-$C_{24}$ fatty acids or esters thereof, preferably a composition of branched $C_{14}$-$C_{22}$ fatty acid esters, more preferably a composition of branched $C_{16}$-$C_{18}$ fatty acid esters according to the invention is used as an emollient.

The invention also relates to a personal care composition comprising a composition of the invention and an active ingredient and/or a pigment or a colorant.

Preferably, the active ingredient is an UV filter, an anti-aging agent and/or a hydrating agent.

Preferably, the personal care composition comprises a composition of branched $C_{10}$-$C_{24}$ fatty acid esters, more preferably a composition of branched $C_{14}$-$C_{22}$ fatty acid esters, still more preferably a composition of branched $C_{16}$-$C_{18}$ fatty acid esters according to the invention.

Preferably, the personal care composition is a lipstick, a lip gloss, a hydrating cream, a sun cream or a mascara.

Compositions of branched $C_{10}$-$C_{24}$ fatty acid esters according to the invention are also useful in home care applications. Also, a home care composition comprises advantageously a composition according to the invention and an active ingredient and/or a surfactant.

Preferably, the home care composition is a detergent.

The invention is further described in the following examples. It will be appreciated that the invention as claimed is not intended to be limited in any way by these examples.

EXAMPLE 1: PROCESS FOR PREPARING A COMPOSITION ACCORDING TO THE INVENTION 1.1 Isomerization of Linear Unsaturated Fatty Acids 1200 grams of fatty acids of high oleic sunflower oil (comprising 83 wt % of oleic acid and 7.3 wt % of linoleic acid) and 60 grams of natural bentonite clay catalyst were placed together in an autoclave. Air was flushed out of the autoclave with nitrogen. While stirring, the mixture was heated to 230° C. This reaction temperature was held for 3 hours, the pressure had built up to 4 barg.

The reaction mixture was then cooled down to 80° C., while removing gaseous components by venting with nitrogen. After adding 18 grams of 75 wt % phosphoric acid, temperature was raised again to 130° C. and pressure was lowered to 60 mbar. These conditions were held for one hour until all water was removed from the product.

The clay catalyst was subsequently removed from the reaction product by vacuum filtration.

1.2 Recovering of the Monomeric Fraction

The monomeric fraction, amounting to substantially 56 wt %, was separated from the oligomeric fraction by distillation up to 260° C. under 2 mbar.

1.3 Purification of the Monomeric Fraction

A hydrogenation step was conducted on the monomer with 0.22% of palladium on carbon catalyst. The product was hydrogenated for 100 minutes at 230° C. and 22 barg hydrogen pressure.

Next, the product was further purified by crystallization in order to isolate the branched fatty acids. For doing this, an aqueous solution containing 1.2 wt % of sodium decyl sulfate and magnesium sulfate was added to the monomeric fraction and the mixture was cooled down to 9° C. The aqueous phase, together with crystals of mainly linear fatty acids, was removed from the branched fatty acids by centrifugation. The branched fatty acids were washed three times with water and a final purification by distillation at 260° C. and 2 mbar was performed.

1.4 Analysis of the Composition According to the Invention

To characterize the composition of the invention obtained after purification step, the carboxylic acids of latter was esterified with methanol. A sample was then analyzed by gas chromatography according to standard ISO 12966-1:2014.

The composition of branched $C_{16}$-$C_{18}$ fatty acids according to the invention obtained comprises:

34.9 wt % of polybranched $C_{18}$ acids;
40.7 wt % of monobranched $C_{18}$ acids;
8.5 wt % of branched $C_{16}$ acids
3.9 wt % of linear and branched $C_8$-$C_{15}$ acid;
3.8 wt % of linear $C_{16}$ acid;
2.9 wt % of linear $C_{18}$ acid;
0.8 wt % of linear $C_{19}$-$C_{22}$ acids;
2.2 wt % of alicyclic carboxylic acids;
1.5 wt % of aromatics;
0.4 wt % of lactones;
0.3 wt % of alkylcyclopentanones.

EXAMPLE 2: POUR POINTS OF A COMPOSITION ACCORDING TO THE INVENTION AND COMPARATIVE COMPOSITIONS 2.1 Content of Different Compositions of Branched Fatty Acids Composition 1a is the composition of branched fatty acids prepared in Example 1;

Comparative composition C1a is a commercial composition of branched fatty acids (Prisorine 3505 from Croda);

Comparative composition C2a is a commercial composition of branched fatty acids (Radiacid 0907 from Oleon);

Contents of each composition were analyzed as in Example 1.4 and results are given in Table 1 below:

TABLE 1

Contents of a composition according to the invention and of comparative compositions

| | Compositions | | |
| --- | --- | --- | --- |
| | 1a (wt %)* | C1a (wt %)* | C2a (wt %)* |
| Linear $C_{16}$ fatty acid | 3.8 | 6.8 | 6.0 |
| Branched $C_{16}$ fatty acids | 8.5 | 5.7 | 3.8 |

TABLE 1-continued

Contents of a composition according
to the invention and of comparative compositions

| | Compositions | | |
|---|---|---|---|
| | 1a (wt %)* | C1a (wt %)* | C2a (wt %)* |
| Linear $C_{18}$ fatty acid | 2.9 | 1.8 | 3.1 |
| Monobranched $C_{18}$ fatty acids | 40.7 | 44.1 | 44.9 |
| Polybranched $C_{18}$ fatty acids | 34.9 | 27.9 | 25.8 |
| Linear and branched $C_8$-$C_{14}$ | 3.9 | 3.1 | 0.8 |
| Linear $C_{19}$-$C_{24}$ fatty acids | 0.8 | 0.6 | 1.4 |
| Alicyclic carboxylic acids | 2.2 | 7.5 | 6.6 |
| Aromatics | 1.5 | 2.5 | 5.1 |
| Alkylcyclopentanones | 0.3 | 0.6 | 0.9 |
| Lactones | 0.4 | 0.0 | 1.3 |

*wt % are based on the total weight of the composition

It can be noticed, that cyclic compound content is much lower in composition 1a (4.4 wt %) than in compositions C1a (10.6 wt %) and C2a (13.9 wt %). In particular, aromatic content and in particular, phenyl carboxylic acid content, is lower. This low aromatic content is particularly appreciated in cosmetic applications. Alicyclic carboxylic acid content is even much lower in composition 1a (2.2 wt %) than in compositions C1a (7.5 wt %) and C2a (6.6 wt %). It is advantageous to have low cyclic hydrocarbon content (e.g. a low alicyclic and aromatic content) since cyclic hydrocarbon have less favorable ecotoxicity and biodegradability properties.

It can also be noticed, that in comparative compositions C1a and C2a, polybranched $C_{18}$ contents are lower than in composition 1a. Weight ratio monobranched/polybranched $C_{18}$ fatty acids is 1.17 for composition 1a, while it is 1.6 for C1a and 1.7 for C2a.

Analysis results further show that branched $C_{16}$ fatty acid content is higher in composition 1a than in compositions C1a and C2a.

2.2 Esterification of Fatty Acids

Composition 1a prepared in Example 1 (85.5 wt %) was esterified with trimethylolpropane (14.5 wt %).

A composition of branched fatty acid esters 1e is obtained that comprises the same type of compounds than in the composition 1a, in an esterified form (except for non-carboxylic acid compounds present in composition 1a which did not react), with the same contents. Esters are a mixture of monoesters (2 wt %), diesters (11 wt %) and triesters (87 wt %) of trimethylolpropane and carboxylic acids of the composition 1a.

Comparative composition C2a (85.5 wt %) was also esterified as composition 1a with trimethylolpropane (14.5 wt %), to form a comparative composition of branched fatty acid esters C2e.

The comparative composition C2e obtained comprises the same type of compounds than in the comparative composition C2a, in an esterified form (except for non-carboxylic acid compounds present in composition 1a which did not react), with the same contents.

2.3 Determination of Pour Points

Pour points were determined according to method described in ASTM D97. Results obtained for each composition of branched fatty acid esters are gathered in Table 2 below:

TABLE 2

Pour points of composition according
to the invention and of comparative composition

| | Cyclic content (wt %) | Weight ratio mono/polybranched $C_{18}$ fatty acid esters | Pour point |
|---|---|---|---|
| Composition 1e | 4.4 | 1.17 | −44° C. |
| Comparative composition C2e | 13.9 | 1.7 | −32° C. |

As can be seen, composition according to the invention with lower cyclic content and a higher polybranched content has a lower pour point.

For applications such as in lubricant field, the lower the pour point the better.

The invention claimed is:

1. A composition of branched $C_{10}$-$C_{24}$ fatty acids or esters thereof, comprising:
   at least 30% by weight of polybranched $C_{10}$-$C_{24}$ fatty acids or esters thereof, and
   1 to 8% by weight of cyclic compounds,
   weight % being given on the total weight of the composition.

2. The composition of claim 1, wherein cyclic compounds comprise alicyclic carboxylic acid(s) or ester(s) thereof, which content ranges from 0.5% to 6% by weight based on the total weight of the composition.

3. The composition of claim 1, comprising at least 15% by weight of monobranched $C_{10}$-$C_{24}$ fatty acids or esters thereof, based on the total weight of the composition.

4. The composition of claim 1, wherein the weight ratio of monobranched/polybranched $C_{18}$ fatty acids or esters thereof, ranges from 0.5 to 1.5.

5. The composition of claim 1, comprising at least 50% by weight of mono and polybranched $C_{10}$-$C_{24}$ fatty acids or esters thereof, based on the total weight of the composition.

6. The composition of claim 1, further comprising 1-25% by weight of linear saturated $C_8$-$C_{24}$ fatty acid(s) or ester(s) thereof, based on the total weight of the composition.

7. A process for preparing a composition of branched $C_{10}$-$C_{24}$ fatty acids from a starting material comprising at least 70% by weight of linear monoethylenically unsaturated $C_{10}$-$C_{24}$ fatty acid(s) based on the total weight of the starting material, comprising the following steps:
   i) isomerizing the linear monoethylenically unsaturated $C_{10}$-$C_{24}$ fatty acid(s) from the starting material, by heating in the presence of a clay catalyst,
   ii) separating the monomeric fraction from the oligomeric fraction formed during step i), and
   iii) purifying the monomeric fraction to obtain the composition of branched $C_{10}$-$C_{24}$ fatty acids.

8. The process of claim 7, wherein the starting material comprises at least 70% by weight of oleic acid based on the total weight of the starting material.

9. The process of claim 7, wherein the starting material comprises at least 5% by weight of linear polyethylenically unsaturated $C_{10}$-$C_{24}$ fatty acid(s) based on the total weight of the starting material.

10. The process of claim 7, wherein the starting material is fatty acids obtained from high oleic sunflower oil, high oleic safflower oil, crambe oil, lunaria oil or olive oil.

11. The process of claim 7, wherein the clay catalyst is a bentonite.

12. A process for preparing a composition of esters of branched $C_{10}$-$C_{24}$ fatty acids, comprising the process for preparing a composition of branched $C_{10}$-$C_{24}$ fatty acids according to claim 7 and a further esterifying step of the composition of branched $C_{10}$-$C_{24}$ fatty acids.

13. A lubricant, a personal care and/or a home care composition comprising the composition of claim 1.

14. The lubricant composition of claim 13, further comprising a base oil.

15. The personal care composition of claim 13, further comprising an active ingredient and/or a pigment or a colorant.

16. The home care composition of claim 13, further comprising an active ingredient and/or a surfactant.

* * * * *